(12) United States Patent
Mizutani et al.

(10) Patent No.: US 6,436,082 B1
(45) Date of Patent: Aug. 20, 2002

(54) ABSORBENT ARTICLE HAVING AN IMPROVED DIFFUSION PROPERTY

(75) Inventors: Satoshi Mizutani; Etsuko Tagami, both of Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 17 days.

(21) Appl. No.: 09/707,392

(22) Filed: Nov. 7, 2000

(30) Foreign Application Priority Data

Nov. 15, 1999 (JP) .......................................... 11-323943

(51) Int. Cl.⁷ ................................................ A61S 13/15
(52) U.S. Cl. ................................ 604/385.101; 264/286; 428/182
(58) Field of Search ................... 604/385.101; 264/286; 428/182

(56) References Cited

U.S. PATENT DOCUMENTS

| | | | |
|---|---|---|---|
| 5,268,213 A | | 12/1993 | Murakami et al. .......... 428/163 |
| 5,476,459 A | * | 12/1995 | Yang .......................... 604/367 |
| 5,514,120 A | * | 5/1996 | Johnston et al. ............ 604/378 |
| 5,527,300 A | * | 6/1996 | Sauer ......................... 604/373 |
| 5,906,879 A | | 5/1999 | Huntoon et al. ............ 428/136 |
| 6,290,685 B1 | * | 9/2001 | Insley et al. .................... 165/6 |

FOREIGN PATENT DOCUMENTS

DE          1 879 601          9/1963

\* cited by examiner

*Primary Examiner*—Andy Falik
(74) *Attorney, Agent, or Firm*—Darby & Darby (57) ABSTRACT

An absorbent article including an absorbent layer and a liquid-permeable surface sheet placed on a liquid-receiving side of the absorbent layer for introducing excreted liquid from the human body to the absorbent layer. The surface sheet is of a corrugated configuration to have valleys and peaks extending in a longitudinal direction of the article and alternately arranged in a transverse direction perpendicular to the longitudinal direction. Each peak is formed with spares parts and dense parts alternately arranged in the longitudinal direction. The surface sheet has a lower fiber density in the sparse parts than in the dense parts.

10 Claims, 8 Drawing Sheets

ABSORBENT ARTICLE HAVING AN IMPROVED DIFFUSION PROPERTY

BACKGROUND OF THE INVENTION

1. Field of the Invention

The present invention relates to an absorbent article, such as a sanitary napkin, a panty liner and a pad for incontinence, and in particular, it relates to an absorbent article in that absorbent property and diffusion property between a surface sheet and an absorbent core are improved to have excellent dry feeling.

2. Description of the Related Art

There have been some absorbent articles including a sanitary napkin and a panty liner in which a skin contacting surface of a surface sheet is of a corrugated configuration to have peaks and valleys alternately arranged so that the surface sheet to contact the skin directly is improved in dry feeling and soft feeling.

However, when the direction along which the peaks and valleys extend (i.e., an orientation direction) is identical with the longitudinal direction of the absorbent article, the corrugated configuration is liable to be resistance against the absorbent article being incurvated in the longitudinal direction. Accordingly, in order to incurvate and deform the absorbent article by pressure from the body upon use, a plurality of creases are necessarily formed on the surface of the peaks to extend in the transverse direction perpendicular to the longitudinal direction. Because the surface sheet is folded at the creases, the surface sheet can be incurvated along the body shape of the user.

In the parts of the surface sheet where the creases are formed, the surface sheet is in contact with the absorbent core located therebelow, but in the parts where the creases are not formed, an excessive force may be applied to separate the absorbent core and the surface sheet. As a result, in the part where the absorbent core and the surface sheet are separated, the amount of liquid remaining in the surface sheet is increased, so that the surface sheet loses dry feeling and provides the user with uncomfortable wet feeling.

In particular, because the pressure from the body does not act uniformly on the whole surface of the surface sheet, the surface sheet is often incurvated with irregular curvature radii. That is, in parts where the pressure from the body is concentrated, the curvature radius becomes small to form a large number of creases, whereas in parts where the pressure from the body acts relatively lightly, the curvature radius becomes large to decrease the number of the creases.

Furthermore, because the peaks and valleys are liable to be irregularly creased, there are cases where the peak plugs the valley, and the flow of an excreted liquid is dammed at a part where the surface sheet is bent at an acute angle.

As described in the foregoing, when creases are irregularly formed on the surface sheet, the part where the surface sheet and the absorbent core are separated and the part where the surface sheet is bent are formed irregularly, and therefore an excreted liquid is insufficiently diffused to cause a problem that the surface sheet has a part exhibiting dry feeling and a part exhibiting no dry feeling.

SUMMARY OF THE INVENTION

An object of the invention is to provide an absorbent article in which a surface sheet can be easily incurvated as a whole so that absorbent property and diffusion property between the surface sheet and an absorbent core are improved to have excellent dry feeling.

According to the invention, there is provided an absorbent article comprising an absorbent layer and a liquid-permeable surface sheet placed on a liquid-receiving side of the absorbent layer for introducing excreted liquid from the human body to the absorbent layer, the surface sheet being of a corrugated configuration to have valleys and peaks extending in a longitudinal direction of the article and alternately arranged in a transverse direction perpendicular to the longitudinal direction, wherein each peak is formed with sparse parts and dense parts alternately arranged in the longitudinal direction, and the surface sheet has a lower fiber density in the sparse parts than in the dense parts.

For example, the dense parts may be formed by compressing the peaks intermittently in the longitudinal direction, so that parts that do not receive the compression between the dense parts are the sparse parts.

It is preferred that the peak is made uneven at the top thereof so that the sparse parts form recessed parts and the dense parts form raised parts.

In the invention, the peaks of the corrugated surface sheet can be easily bent due to the presence of the sparse parts having a low fiber density. In addition, because the sparse parts are formed along the peaks of the corrugated surface sheet, the surface sheet can be incurvated as a whole by bending each peak at the sparse parts. Therefore, the peaks are not forcibly bent at the dense parts, so that the surface sheet and the absorbent core are prevented from locally separating by an excessive force. As a result, the liquid permeability of the surface sheet and the absorbent core can be prevented from lowering, and an excreted liquid received by the surface sheet can be effectively led to the absorbent core.

If the sparse parts are recessed toward the absorbent core (i.e., lowered than the dense part), the peaks can be bent at the sparse parts more easily.

In the above, it is preferred that the sparse part has a dimension (w1) in the longitudinal direction of from 1 to 5 mm.

It is preferred that the sparse part has a depth dimension (d2) from the surface of the dense part toward the absorbent core of from 0.5 to 3 mm.

It is preferred that the sparse parts are arranged with a pitch (p) in the longitudinal direction of from 3 to 15 mm.

Owing to the dimensions, a wearer hardly receives uncomfortable feeling due to the unevenness, and the separation of the surface sheet and the absorbent core can be effectively prevented.

The sparse parts may be staggered in the longitudinal direction, between two adjacent peaks. That is, the sparse parts may be arranged in such a manner that one sparse part formed on one peak is positioned between two sparse parts formed on another peak adjacent thereto in the transverse direction.

The sparse parts may be arranged to surround a prescribed region of the surface sheet.

The sparse parts may be formed as concentrated in a prescribed region of the surface sheet.

In the above, it is also preferred that, in each valley, there is provided at least one connecting part to connect between two adjacent peaks.

Owing to the structure, soft feeling of the surface sheet can be maintained, and the shape thereof can be prevented from losing.

BRIEF DESCRIPTION OF THE DRAWINGS

FIGS. 4A, 4B, 4C and 4D are perspective views showing embodiments of arrangements of sparse parts on a surface sheet, in which

FIGS. 8A, 8B and 8C are cross sectional views showing the state where the upper plate and the lower plate are interfitted to each other, in which

DESCRIPTION OF THE PREFERRED EMBODIMENTS

The invention will be described in detail with reference to the drawings.

Figure 1:
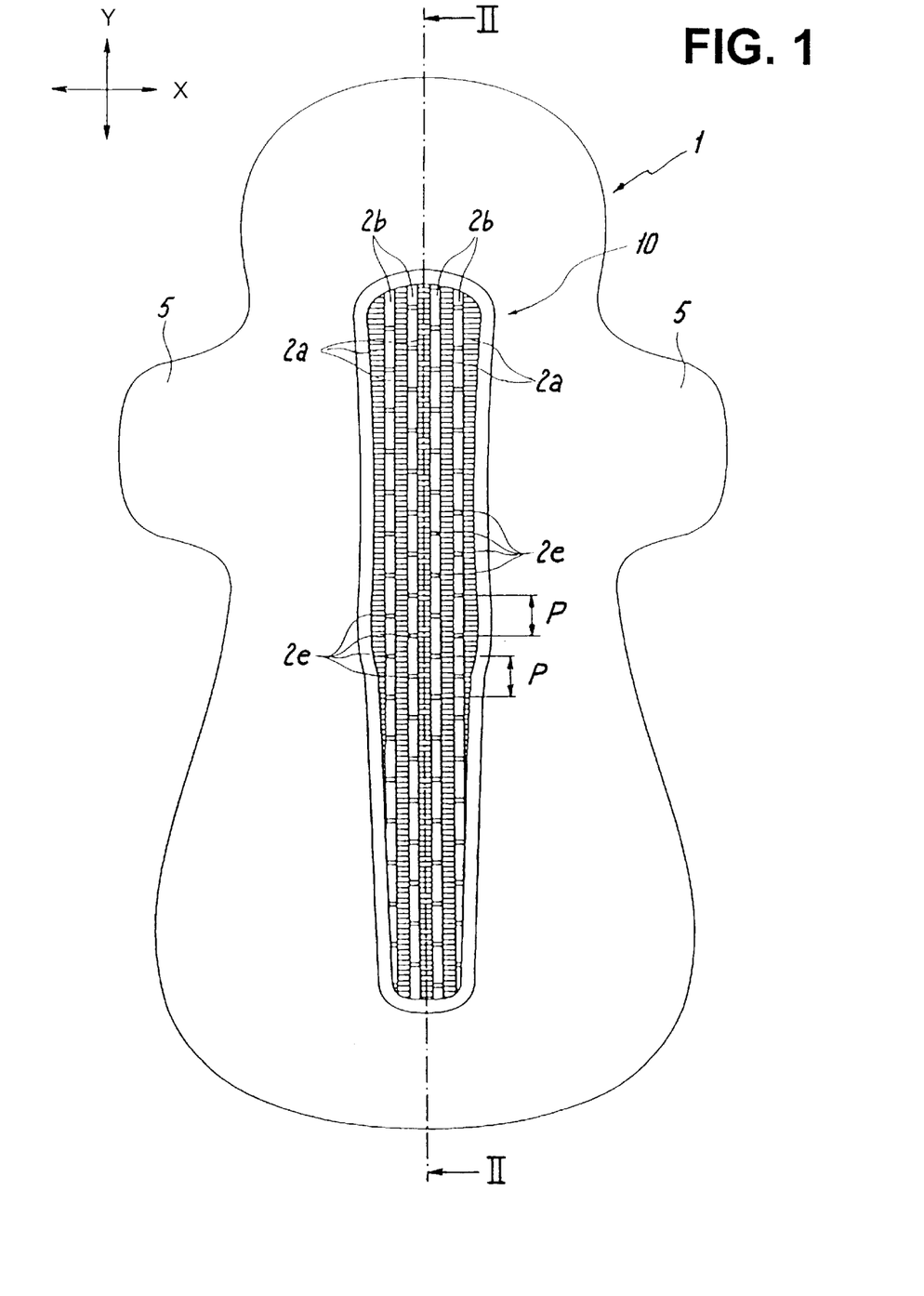
FIG. 1 is a plan view showing an absorbent article according to one embodiment of the invention.
Figure 2:
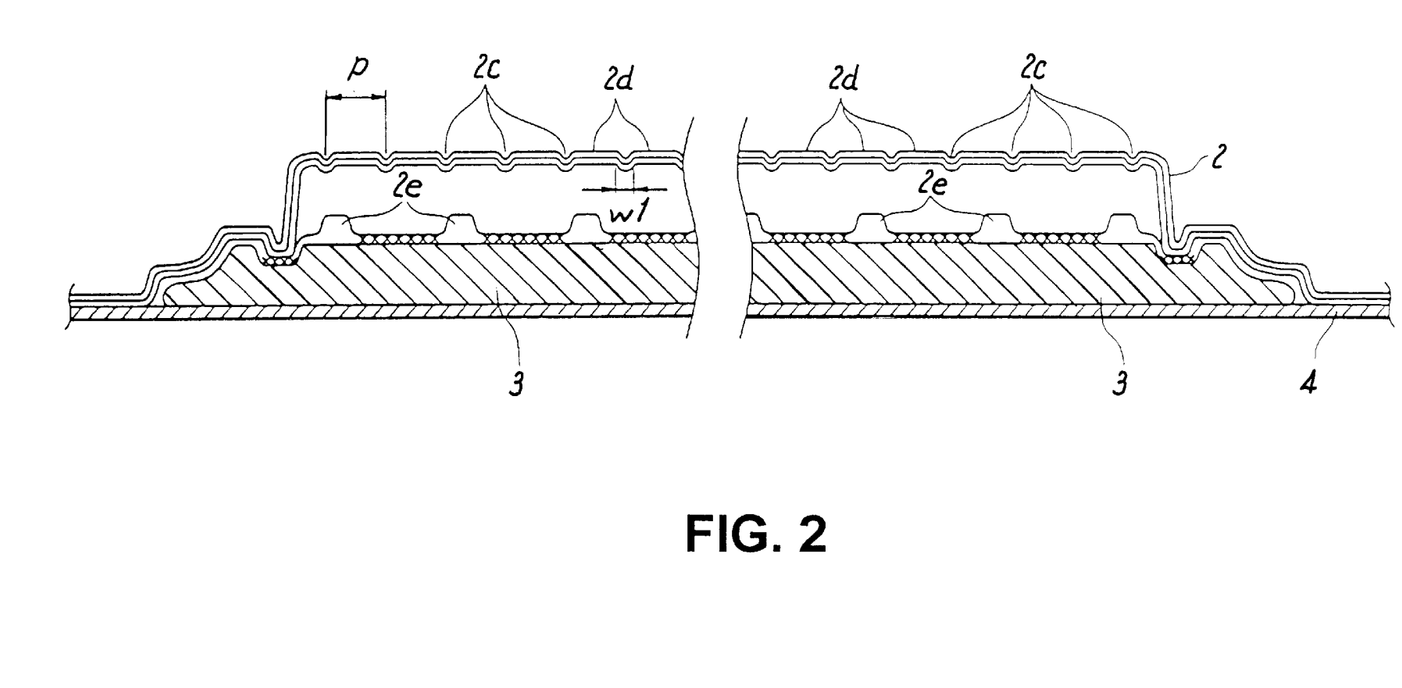
FIG. 2 is a partial cross sectional view of FIG. 1 on line II—II.
Figure 3:
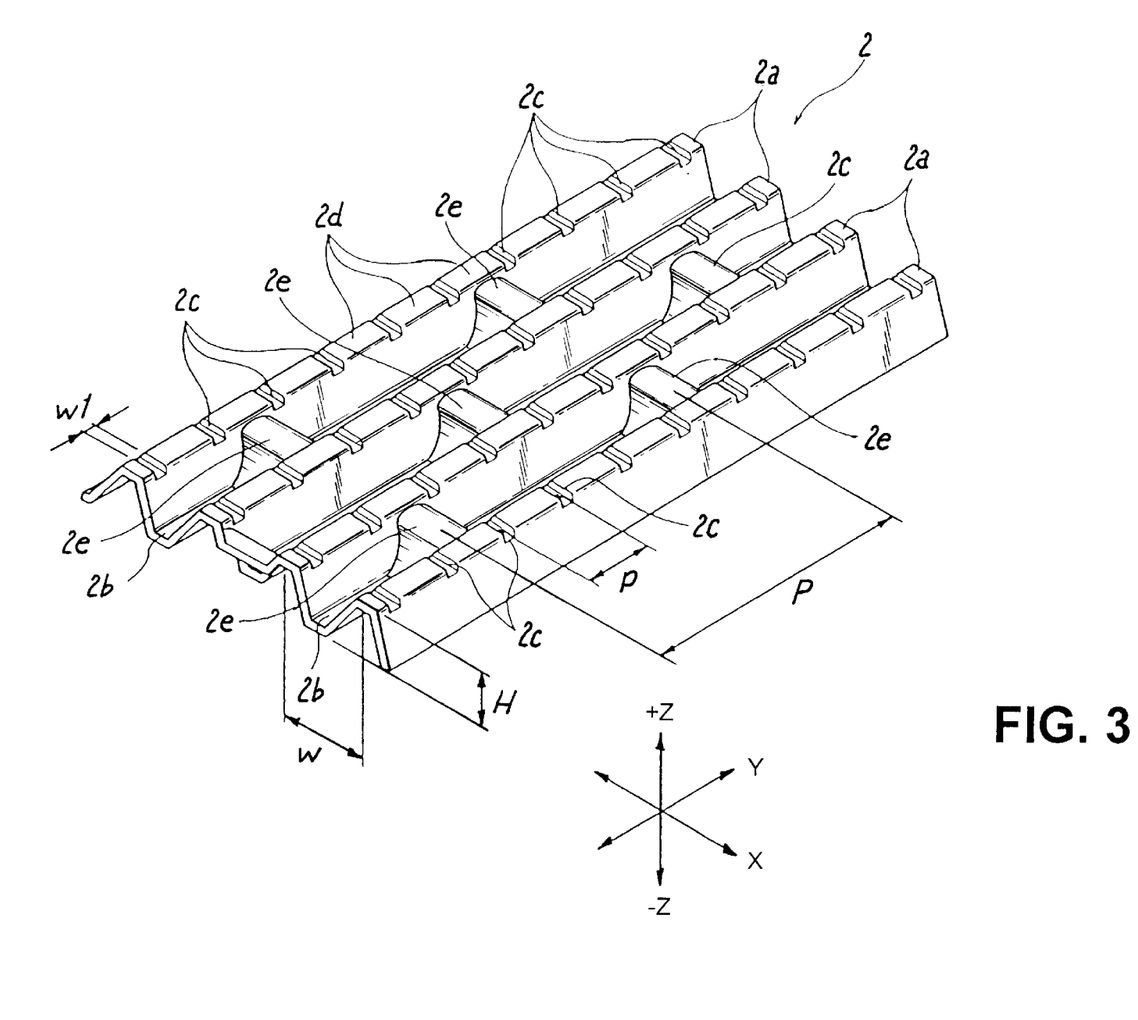
FIG. 3 is a perspective view showing the fragmentary detail of a surface sheet of the absorbent article shown in FIG. 1.

FIG. 1 is a plan view showing an absorbent article according to one embodiment of the invention, FIG. 2 is a cross sectional view of FIG. 1 on line II—II (partially omitted), and FIG. 3 is a perspective view showing the fragmentary detail of a surface sheet of the absorbent article shown in FIG. 1.

As shown in FIG. 1, a skin contacting part 10 for receiving a liquid excreted from the body is formed at the center of a sanitary napkin (absorbent article) 1. As shown in FIG. 2, the sanitary napkin 1 is constructed to include a surface sheet 2, an absorbent core 3 and a back sheet 4. On both sides of the skin contacting part 10, side flaps 5 and 5 are provided.

The surface sheet 2 may be made of any suitable sheet material. Examples of the sheet material include: nonwoven fabric such as air-through nonwoven fabric, point-bonded nonwoven fabric and spun-bonded nonwoven fabric produced by accumulating synthetic fibers, such as of PE (polyethylene), PET (polyethylene terephthalate), etc., or composite fibers, such as of PE/PET, PE/PP (polypropylene), etc., and making the accumulated fibers into a sheet form by thermal welding; a porous film formed with a number of pores and laminated with a fibrous sheet on the skin contacting side thereof; and a porous fibrous sheet formed with a number of pores. These sheet materials may be used alone as a single-layer sheet or may be used in combination as a multi-layer sheet formed by laminating two or more sheets. The constituent fibers for the surface sheet 2 preferably have a fineness in a range of from 1.1 to 6.6 dtex. If it is less than 1.1 dtex, the amount of liquid remaining due to the capillary action is increased to give wet feeling to the wearer. If it exceeds 6.6 dtex, hard and rough feeling is given. The basis weight (This may be referred to as "Metsuke") of the surface sheet 2 is preferably in a range of from 20 to 120 g/m². If it is less than 20 g/m², the surface sheet cannot provide sufficient elasticity to the corrugated configuration thereof and is liable to lose shape. If it exceeds 120 g/m², it becomes too rigid.

In the case where the surface sheet 2 is a multi-layer sheet formed by adhering the entire surfaces of the plurality of sheets of nonwoven fabric, the adhesion strength between the upper layer (upper sheet) and the lower layer (lower sheet) in CD (Cross Direction) is preferably 0.49 N/inch (50 g/inch) or more, so as to secure the durability upon use. When the adhesion strength is less than 0.49 N/inch (50 g/inch), there tend to be cases causing a problem in that the upper layer is peeled to float or is broken.

When the entire surfaces of the upper layer and the lower layer are adhered, the strength between the sheets is increased to improve the durability, as described above. However, on the other hand, the finish of the surface sheet thus laminated tends to be stiff. In such a case, it is preferred that the upper and lower layers of a corrugated configuration are adhered and fixed to each other not in the peaks but only at the bottom parts of the valleys, whereby the peaks to come into contact with the skin directly can be finished more softly.

In the sanitary napkin 1 shown in FIG. 1 to FIG. 3, the surface sheet 2 is made of a multi-layer sheet formed by laminating the plurality of sheets of nonwoven fabric. The surface sheet 2 is formed to have a corrugated configuration (i.e., wavy shape), in which valleys 2b having a concave cross section and peaks 2a having a convex cross section extend in the longitudinal (Y) direction and are alternately arranged in the transverse (X) direction. The bottom parts of the valleys 2b and the surface of the absorbent core 3 are adhered and fixed to each other at the positions indicated with symbols (x) in FIG. 2.

The adhesion between the bottom parts of the valleys 2b and the surface of the absorbent core 3 can be conducted, for example, with a hot melt adhesive. For application of the hot melt adhesive, use can be made of a silicone roll having the same shape as the peaks 2a and the valleys 2b. The roll is applied with the hot melt adhesive in a bead form, inside the valleys thereof, and is then made in contact with the back surface of the surface sheet 2 (the surface directed to the -Z direction) to mach the wavy shape thereof and is trundled, whereby the adhesive can be transferred to the back surface of the valleys 2b of the surface sheet 2. Thus, only the valleys 2b of the surface sheet 2 can be adhered to the absorbent core 3, while preventing the peaks 2a from adhering to each other.

As shown in FIG. 3, the distance H (height in the Z direction) between the top of the peak 2a and the bottom part of the valley 2b is preferably from 1 to 10 mm, and more preferably from 2 to 6 mm. The width W between the peaks 2a, 2a or the valleys 2b, 2b arranged alternately is preferably from 1 to 15 mm, and more preferably from 2 to 10 mm.

On the surface of the peak 2a, sparse parts 2c and dense parts 2d are alternately formed to line with a constant interval in the longitudinal direction. The sparse parts 2c are recessed into a concave shape, i.e., lowered than the dense parts 2d in the -Z direction toward the absorbent core 3, and are formed as extending in the transverse (X) direction in a strip form. The dense parts 2d are formed by heating and/or compression by the means described later and have a density of fibers per unit volume (hereinafter referred to as a fiber density) higher than that of the sparse parts 2c of the surface sheet 2.

The pitch p of the sparse parts 2c in the longitudinal direction is preferably from 3 to 15 mm, and more preferably from 3 to 10 mm. The depth dimension d2 of the sparse parts 2c in the −Z direction is preferably in a range of from 0.5 to 3 mm from the dense parts 2d (top) of the peak 2a toward the absorbent core 3 from the standpoints of bumpy feeling given to the wearer and separation between the surface sheet 2 and the absorbent core 3. The dimension w1 of the sparse parts 2c in the longitudinal direction is preferably from 1 to 5 mm.

The sparse parts 2c preferably have such a shape that when viewed from the longitudinal cross section (the same direction as FIG. 2), the shape from the dense part 2d to the bottom part of the sparse part 2c is not perpendicularly steep-up but forms a curved surface. Owing to such a shape, the dense parts 2d of the surface sheet 2 in contact with the skin are prevented from giving harsh feeling to the wearer. In order to attain the shape, the shape of the edge of the dense part forming part 22c of the lower plate 22 described later is formed to have a taper form (see FIG. 7 and FIG. 8C).

In the sanitary napkin 1 having the surface sheet 2 with such a configuration, when a pressure from the body is applied from the upper side (+Z) to the lower side (−Z) of the surface sheet 2, the center part of the surface sheet 2 is caved with respect to the both ends thereof, whereby the surface sheet 2 is incurvated to a concave form. At this time, the individual sparse parts 2c are bent and approach each other, so that the surface sheet 2 is incurvated as a whole. The peaks 2a of the surface sheet 2 are bent only at the sparse parts 2c, but they are not bent at the dense parts 2d. That is, the peaks 2a can be uniformly incurvated by dispersing the pressure from the body to the sparse parts 2c, and therefore, no crease is formed in the dense parts 2d. This can prevent the separation of the surface sheet 2 from the surface of the absorbent core 3. As a result, the permeability (transmissibility) of a liquid from the surface sheet 2, more particularly from the peaks 2a of the surface sheet 2 to the absorbent core 3 is not lost, so that the amount of the liquid remaining in the surface sheet 2 can be made less. Thus, excellent dry feeling can be obtained, and comfortable feeling can always be given to the wearer.

In the surface sheet 2 shown in FIG. 3, a plurality of connecting parts 2e are formed inside one valley 2b with a prescribed pitch P, so as to connect between the adjacent peaks 2a, 2a at both sides of the valley 2b. Due to the presence of the connecting parts 2e, the deformation amount of the surface sheet 2 caused by the pressure from the body can be minimized. The elasticity of the connecting parts 2e functions as a restoring force to recover the original state of the surface sheet 2 upon releasing the pressure from the body. Therefore, since the surface sheet 2 has an excellent recovering force, the shape thereof is not lost even when the wearer gets hard exercise.

The sparse parts 2c may be arranged on the surface sheet 2 in the following manner.

Figure 4A:
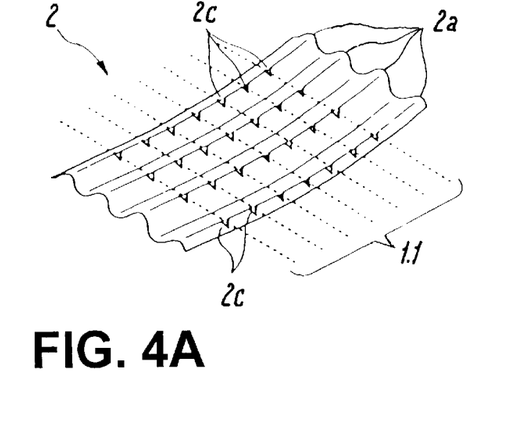
FIG. 4A shows the first pattern.
Figure 4B:
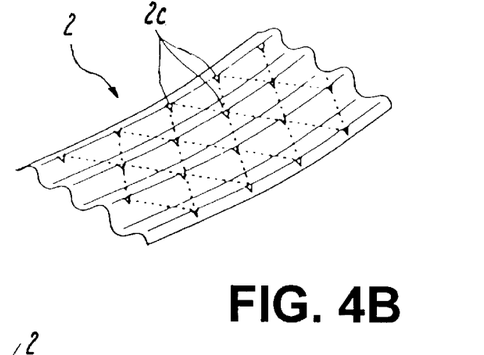
FIG. 4B shows the second pattern.
Figure 4C:
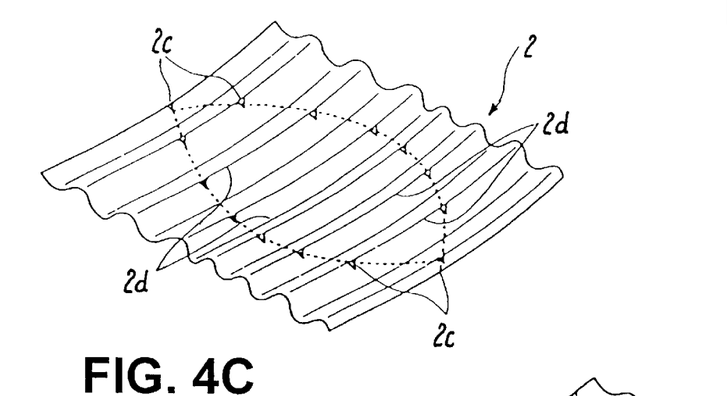
FIG. 4C shows the third pattern.
Figure 4D:
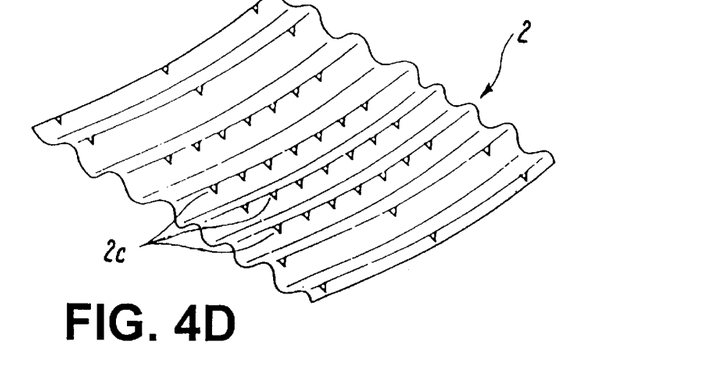
FIG. 4D shows the fourth pattern.

FIGS. 4A, 4B, 4C and 4D are perspective views showing embodiments of arrangements of the sparse parts on the surface sheet, in which FIG. 4A shows the first pattern, FIG. 4B shows the second pattern, FIG. 4C shows the third pattern, and FIG. 4D shows the fourth pattern.

In the first pattern (linear array) shown in FIG. 4A, the peaks 2a extend in the longitudinal (Y) direction of the surface sheet 2, and a plurality of sparse parts 2c are arranged in the transverse (X) direction perpendicular to the peaks 2a. In the first pattern (linear array), the sparse parts 2c form a plurality of bent lines L1 extending parallel to each other and arranged at regular intervals. When the surface sheet 2 is incurvated to make the center of curvature radius directed to the side of the skin contacting part (+Z side) of the surface sheet 2, it can be easily bent at the bent lines L1. Thus, the resistance caused by the arrangement of the peaks 2a can be relaxed.

In the second pattern (staggered array) shown in FIG. 4B, the sparse parts 2c are arranged alternately with respect to the adjacent peaks 2a in the transverse direction. That is, the sparse parts 2c are staggered in the longitudinal direction, between the adjacent peaks 2a in the transverse direction. In the second pattern, a plurality of bent lines connecting the sparse parts 2c are formed in a polygonal line form. The resistance caused by the arrangement of the peaks 2a can also be relaxed with the bent lines.

In the third pattern (round array) shown in FIG. 4C, the sparse parts 2c are formed on the peaks 2a inside the prescribed region of the surface sheet 2 in a circular or elliptical form. Owing to such a structure, the dense parts 2d having high liquid permeability are formed inside the region. On the other hand, the sparse parts 2c in the periphery outside the region have higher retaining property of a liquid than the dense parts 2d. It is visually confirmed that the interior of the prescribed region is a part having a high absorbent effect of an excreted liquid. Because the sparse parts 2c inside the region have low liquid permeability, unnecessary diffusion of the excreted liquid can be suppressed.

In the fourth pattern (pattern with dense center and sparse periphery) shown in FIG. 4D, the sparse parts 2c are formed as concentrated in a prescribed region (substantially the central part) of the surface sheet 2. In the surface sheet 2, as a result of concentration of the sparse parts 2c of low permeability in the central part thereof, the retaining ability of an excreted liquid in the central part can be improved. The diffusion property of the excreted liquid in the transverse direction of the surface sheet 2 can be improved by surrounding the periphery of the central part with the dense parts 2d having a high fiber density. As a result, the absorption rate to the absorbent core 3 can be increased.

A production process of the surface sheet will be described below.

Figure 5:
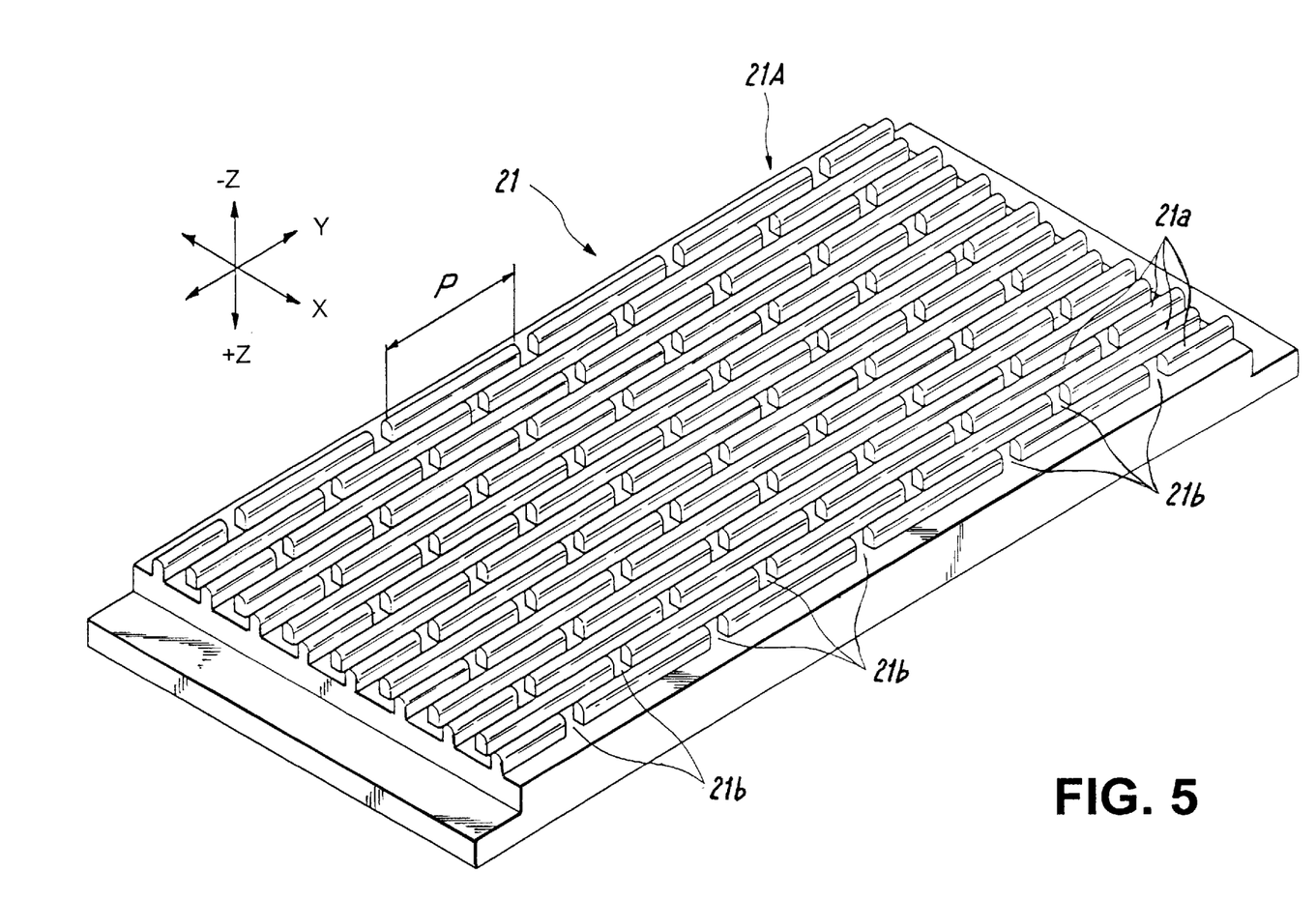
FIG. 5 is a perspective view showing an upper plate for producing the surface sheet.
Figure 6:
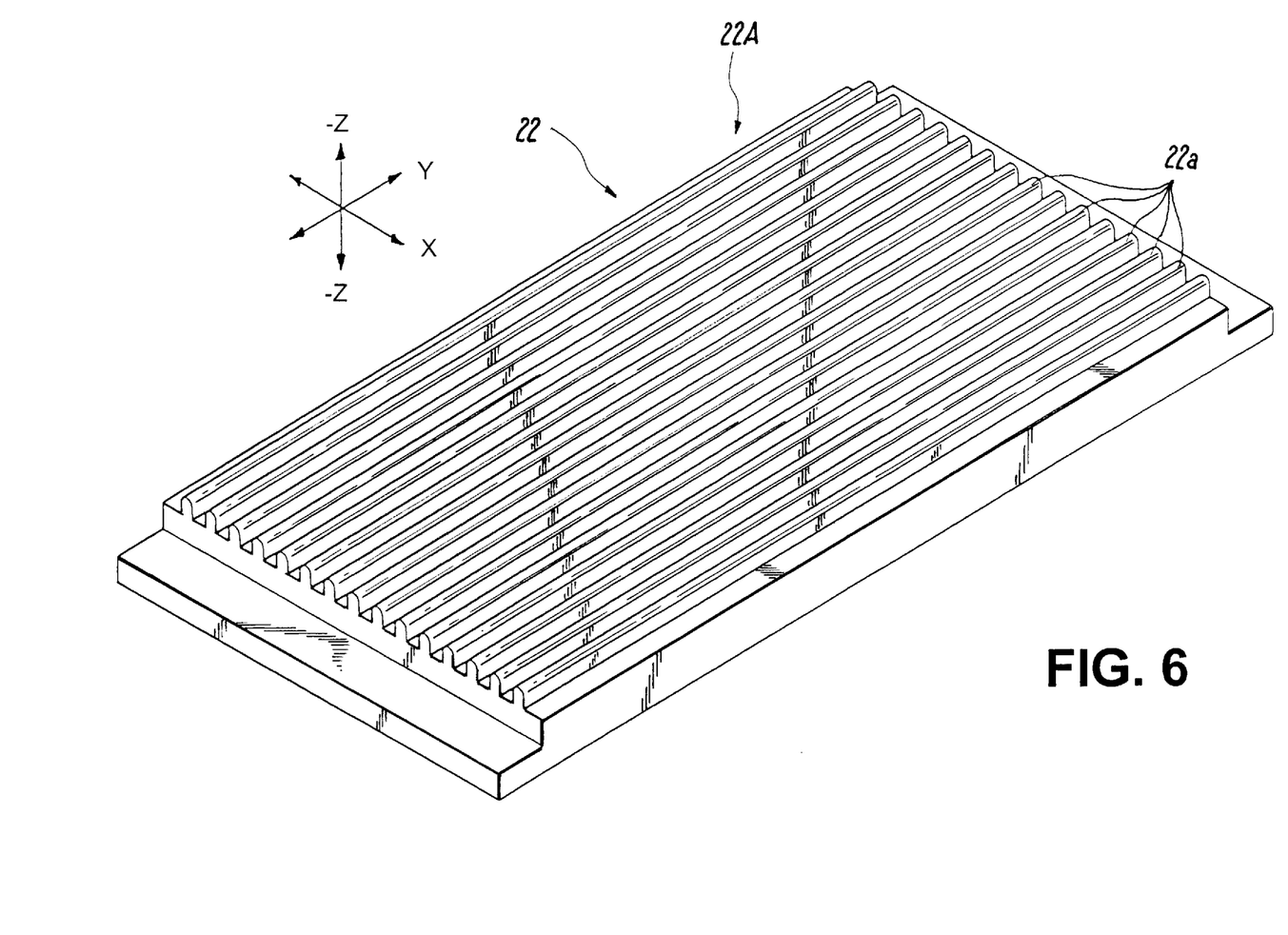
FIG. 6 is a perspective view showing a lower plate for producing the surface sheet.

FIGS. 5 and 6 show a mold for producing the surface sheet, in which FIG. 5 shows an upper plate, and FIG. 6 shows a lower plate.

As shown in FIG. 5, a plurality of convex ribs 21a having a prescribed length are formed in the longitudinal direction on a press surface 21A of the upper plate 21. In the upper plate 21, gaps 21b having a prescribed length are formed between the convex ribs 21a adjacent to each other in the longitudinal (Y) direction. The convex ribs 21a are also arranged in the transverse (X) direction, and the distances between the rows adjacent to each other is set at a constant width. The gaps 21b are formed as staggered in the longitudinal direction in the rows adjacent to each other.

Figure 7:
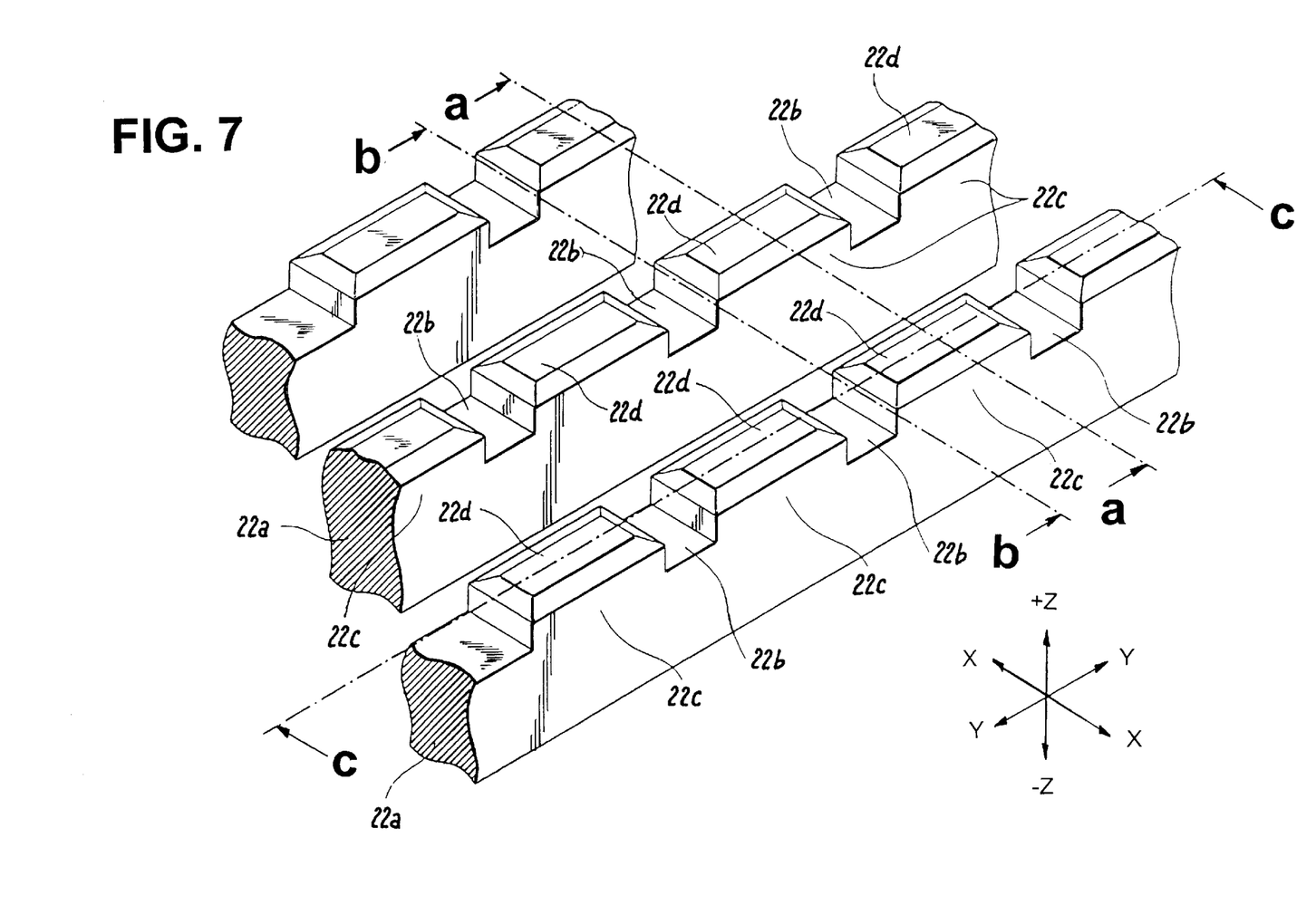
FIG. 7 is an enlarged perspective view showing the fragmentary detail of ribs on the lower plate.

On a press surface 22A of the lower plate 22 shown in FIG. 6, on the other hand, there are formed ribs 22a extending in the longitudinal direction and arranged in the transverse direction in rows. FIG. 7 is a perspective view showing the detail of the ribs on the lower plate. As shown in FIG. 7, on the upper surface of the ribs 22a, sparse part forming parts 22b having a concave form, and dense part forming parts 22c having a convex form are alternately formed. That is, the sparse part forming parts 22b are formed at regular intervals. The top parts of the dense part forming part 22c are compression parts 22d.

Figure 8A:
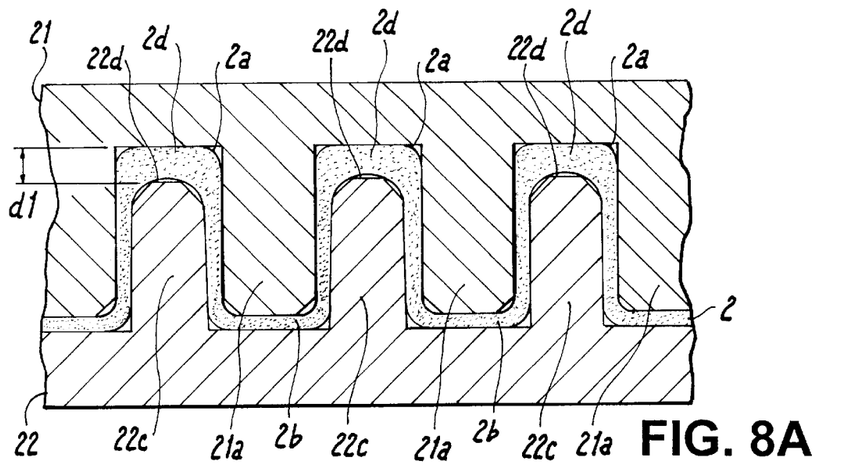
FIG. 8A is a cross sectional view in the transverse direction of a dense part forming part of the lower plate and the upper plate.
Figure 8B:
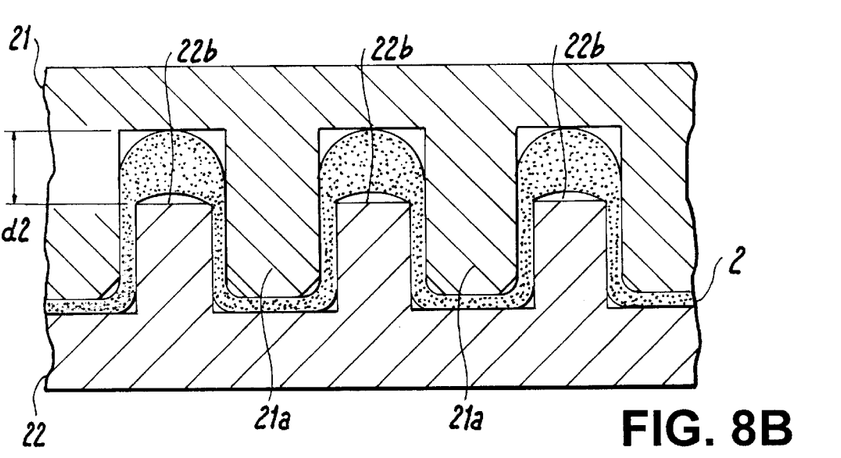
FIG. 8B is a cross sectional view in the transverse direction of a sparse part forming part of the lower plate and the upper plate.
Figure 8C:
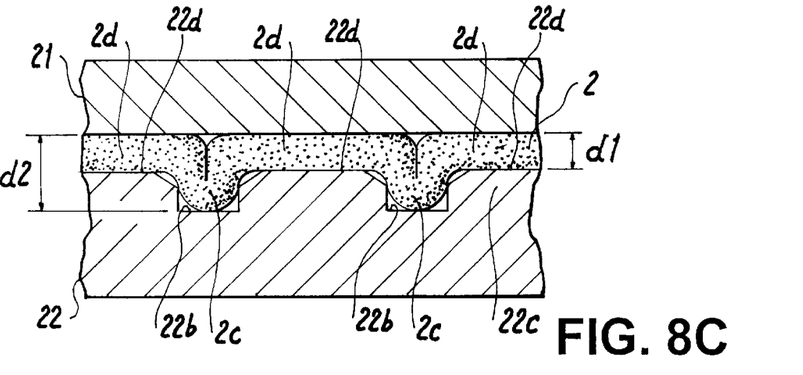
FIG. 8C is a cross sectional view in the longitudinal direction of the rib of the lower plate (on line c—c in FIG. 7) and the upper plate.

FIGS. 8A, 8B and 8C are cross sectional views showing the state where the upper plate and the lower plate are interfitted to each other, in which FIG. 8A is a cross sectional view in the transverse direction of the dense part forming part of the lower plate (on line a—a in FIG. 7) and the upper plate, FIG. 8B is a cross sectional view in the transverse direction of the sparse part forming part of the lower plate (on line b—b in FIG. 7) and the upper plate, and FIG. 8C is a cross sectional view in the longitudinal direction of the rib of the lower plate (on line c-c in FIG. 7) and the upper plate.

When the upper plate 21 and the lower plate 22 are superposed on each other in such a state that the press surfaces 21A and 22A face each other, the convex ribs 21a of the upper plate 21 each is interfitted between the ribs 22a of the lower plate 22. When nonwoven fabric intervenes between the plates as shown in FIG. 8A at this time, the surface sheet 2 having the corrugated configuration can be formed by the ribs 22a and the convex ribs 21a.

The sparse parts 2c and the dense parts 2d are simultaneously formed alternately on the top parts of the peaks 2a along the longitudinal direction as shown in FIGS. 2 and 3. That is, as shown in FIGS. 8A and 8C, because the distance d1 between the compression part 22d of the dense part forming part 22c of the lower plate 22 and the bottom between the convex ribs 21a of the upper plate 21 is set at a value smaller than the thickness of the nonwoven fabric (surface sheet), the top parts of the nonwoven fabric (surface sheet) are compressed by the compression parts 22d of the dense part forming part 22c. As a result, the dense parts 2d having a high fiber density can be formed at the top parts of the surface sheet 2. As shown in FIGS. 8B and 8C, on the other hand, the distance d2 (depth dimension of the sparse part) between the bottom between the convex ribs 21a of the upper plate 21 and the sparse part forming part 22b of the lower plate 22 is set at a value larger than the distance d1 on the side of the dense part forming part 21c. Therefore, the sparse parts 2c having a low fiber density suffering relatively light compression are formed at the top parts of the surface sheet 2.

In addition, the connecting parts 2e in the valleys 2b of the surface sheet 2 shown in FIG. 2 can be formed by the gaps 21b provided in the upper plate 21, whereby two peaks 2a, 2a at the sides of each valley 2b can be connected to each other.

In the lower plate 22 shown in FIG. 7, since the sparse part forming parts 22b are formed with a constant pitch p in the longitudinal direction, the surface sheet having the first pattern (linear array) shown in FIG. 4A can be formed. When the sparse part forming parts 22b on the ribs 22a are formed alternately (staggered pattern), the surface sheet having the second pattern shown in FIG. 4B can be formed. When the sparse part forming parts 22b are formed in the ribs 22a on the press surface 22A of the lower plate 22 in a circular or elliptical form, the surface sheet having the third pattern shown in FIG. 4C can be formed. Furthermore, when the sparse part forming parts 22b are concentrated in the central part of the press surface 22A of the lower plate 22, the surface sheet having the fourth pattern shown in FIG. 4D can be formed.

In order to mass-produce the surface sheet, rollers are employed. That is, the upper plate 21 and the lower plate 22 are formed into an upper roller and a lower roller, respectively, each having a roll form, and when a strip of nonwoven fabric is passed between the upper roller and the lower roller, the surface sheet 2 shown in FIG. 2, FIG. 3 and FIGS. 4A to 4D can be continuously formed.

At this time, when the nonwoven fabric is pressed under the condition where the rollers are heated to a temperature of from 60 to 160° C., the surface sheet 2 having higher stiffness, i.e., difficult to lose the shape thereof, can be formed. It is also possible that the nonwoven fabric before passing between the rollers is subjected to a pre-heating treatment, and examples of the pre-heating treatment include passing through pre-heating rollers or blowing hot air.

While the absorbent article of the invention has been described with reference to a sanitary napkin, it may also be embodied in a panty liner, a pad for incontinence and the like.

As has been described in detail, according to the invention, the surface sheet can be incurvated and deformed at the sparse parts formed on the peaks, so that the surface sheet is not forcedly bent at the dense parts other than the sparse parts. Therefore, no excessive force is applied between the surface sheet and the absorbent core, and the separation thereof can be prevented. As a result, deterioration of the liquid permeability and the diffusion property between the surface sheet and the absorbent core is prevented to maintain dry feeling of the surface sheet.

Here, "comprises/comprising" when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorbent article comprising an absorbent layer and a liquid-permeable surface sheet placed on a liquid-receiving side of the absorbent layer for introducing excreted liquid from the human body to the absorbent layer, the surface sheet being of a corrugated configuration to have valleys and peaks extending in a longitudinal direction of the article and alternately arranged in a transverse direction perpendicular to the longitudinal direction, wherein each peak is formed with sparse parts and dense parts alternately arranged in the longitudinal direction, and the surface sheet has a lower fiber density in the sparse parts than in the dense parts.

2. The absorbent article as set forth in claim 1, wherein the dense parts are formed by compressing the peaks intermittently in the longitudinal direction, such that the sparse parts that do not receive the compression between the dense parts.

3. The absorbent article as set forth in claim 2, wherein the peak is made uneven at the top thereof so that the sparse parts form recessed parts and the dense parts form raised parts.

4. The absorbent article as set forth in claim 3, wherein the sparse part has a dimension (w1) in the longitudinal direction of from 1 to 5 mm.

5. The absorbent article as set forth in claim 4, wherein the sparse part has a depth dimension (d2) from the surface of the dense part toward the absorbent layer of from 0.5 to 3 mm.

6. The absorbent article as set forth in claim 5, wherein the sparse parts are arranged with a pitch (p) in the longitudinal direction of from 3 to 15 mm.

7. The absorbent article as set forth in claim 6, wherein the sparse parts are staggered in the longitudinal direction, between two adjacent peaks.

8. The absorbent article as set forth in claim 1, wherein the sparse parts are arranged to surround a prescribed region of the surface sheet.

9. The absorbent article as set forth in claim 1, wherein the sparse parts are formed as concentrated in a prescribed region of the surface sheet.

10. The absorbent article as set forth in claim 1, wherein in each valley, there is provided at least one connecting part for interconnecting two adjacent peaks.

\* \* \* \* \*